United States Patent
Jensen et al.

(10) Patent No.: US 8,986,357 B2
(45) Date of Patent: Mar. 24, 2015

(54) BILATERAL LAMINA IMPLANT

(75) Inventors: Harm-Iven Jensen, Noer (DE); Helmut D. Link, Hamburg (DE)

(73) Assignee: Facet-Link Inc., Rockaway, NJ (US)

( * ) Notice: Subject to any disclaimer, the term of this patent is extended or adjusted under 35 U.S.C. 154(b) by 276 days.

(21) Appl. No.: 13/247,617

(22) Filed: Sep. 28, 2011

(65) Prior Publication Data
US 2012/0078304 A1    Mar. 29, 2012

Related U.S. Application Data

(60) Provisional application No. 61/387,315, filed on Sep. 28, 2010.

(30) Foreign Application Priority Data

Sep. 28, 2010 (EP) .................................... 10011155

(51) Int. Cl.
*A61B 17/70* (2006.01)
*A61B 17/88* (2006.01)

(52) U.S. Cl.
CPC ......... *A61B 17/7074* (2013.01); *A61B 17/7071* (2013.01); *A61B 17/888* (2013.01)
USPC .......................................... 606/326; 606/324

(58) Field of Classification Search
CPC ..................... A61B 17/7071; A61B 2017/025; A61B 2017/681; A61B 17/7047; A61B 17/025; A61B 17/68; A61B 2017/0256
USPC ............................ 606/324, 90, 251, 252, 326
See application file for complete search history.

(56) References Cited

U.S. PATENT DOCUMENTS

| 2003/0032959 A1* | 2/2003 | Yeh ................................. 606/61 |
| 2005/0203534 A1* | 9/2005 | Mommaerts .................... 606/90 |
| 2005/0267475 A1* | 12/2005 | Miller, III ....................... 606/69 |
| 2006/0241591 A1* | 10/2006 | Biscup et al. ................... 606/60 |
| 2009/0081602 A1* | 3/2009 | Ayan ................................. 433/7 |
| 2009/0240280 A1* | 9/2009 | Wang et al. .................... 606/207 |
| 2009/0248076 A1* | 10/2009 | Reynolds et al. .............. 606/246 |
| 2010/0057127 A1 | 3/2010 | McGuire et al. |
| 2010/0106190 A1 | 4/2010 | Linares |
| 2010/0152854 A1 | 6/2010 | Slivka et al. |

FOREIGN PATENT DOCUMENTS

WO    WO-2006/104487    10/2006

OTHER PUBLICATIONS

European Search Report mailed Mar. 7, 2011, directed to European Application No. 10011155.8; 9 pages.

* cited by examiner

*Primary Examiner* — Eduardo C Robert
*Assistant Examiner* — Julianna N Harvey
(74) *Attorney, Agent, or Firm* — Morrison & Foerster LLP (57) ABSTRACT

A reinforcing implant for the lamina of a vertebra includes a transverse support, one anchoring device for the right-hand side and one anchoring device for the left-hand side of the lamina of the vertebra. An expansion element with a guide device and cheek elements is provided, the cheek elements being mounted to be longitudinally movable along the guide device. Bearing surfaces for the lamina are formed on outer faces of the cheek elements directed away from each other, and a return stop for the cheek elements is provided. At least one of the cheek elements is provided with an aligning device for modifying the orientation of its bearing surface relative to the guide device. In this way, a secure anchoring of the reinforcing implant on the resected surfaces produced during a laminectomy can be achieved, with precise adaptation of the reinforcing implant to the actual anatomical conditions following the laminectomy.

30 Claims, 8 Drawing Sheets

BILATERAL LAMINA IMPLANT

REFERENCE TO RELATED APPLICATION

This application claims the priority of European Patent Application No. 10 011 155, filed Sep. 28, 2010, and of U.S. Provisional Application No. 61/387,315, the entire contents of which are incorporated herein by reference.

FIELD OF THE INVENTION

Background of the Invention

The invention relates to a bilateral reinforcing implant for the lamina of a vertebra, comprising a transverse support and one anchoring device for the left-hand side and one anchoring device for the right-hand side of the lamina of the vertebra.

The spinal column forms a central structural element of the human skeleton. It comprises a multiplicity of vertebrae arranged one above another in order to transmit loads and interconnected in an articulated manner in order to permit movements. The vertebrae of the spinal column are not identical and instead differ in shape depending on where they are located in the spinal column. They do however have some features in common. Thus, each vertebra has a solid vertebral body with two osseous projections (pedicles) which extend laterally and to the rear and which, in their rear part, are in turn connected by an osseous arch. In the connection area, this osseous arch is shaped as a broad plate (lamina) and has, at its center, a rearwardly protruding spinous process. The spinous process and two further transverse processes on the side surfaces of the pedicles form articulation points for muscles and ligaments. In the area where the pedicles merge into the broad lamina, an upper and a lower articulating process are arranged on each side of the vertebra. These each form part of a facet joint with an adjacent upper or lower vertebra. Moreover, for the load transmission of the vertebrae, an intervertebral disk is arranged in each case between the vertebral bodies of adjacent vertebrae and fills the space between the relatively flat cover surfaces of the adjacent vertebral bodies. The area bounded by the rear side of the vertebral body and by the osseous arch (vertebral arch) forms a hollow space in which nerve fibers running parallel to the spinal column are accommodated.

Diseases or injuries can lead to many different forms of back pain. Common causes are, in particular, defects of the intervertebral disk or of the facet joints, or the nerve fibers extending through the hollow space becoming pinched or trapped. In the latter case in particular, it is known that this pressure is often generated by osseous growths forming in the area of the hollow space. In order to combat the pain, the pressure must be reduced and, for this purpose, the growth has to be removed. For this purpose, an access route to the hollow space is usually created through the rear side of the vertebral arch, that is to say generally through the lamina, and the growths causing the problems are removed from there by means of suitable instruments known per se. When access is made on only one side of the vertebra, that is to say in one area of the lamina to the side of the spinous process, this is referred to as a unilateral approach, whereas, when access is made on both sides of the spinous process and the latter is then removed, this is referred to as a bilateral approach. In this procedure called a laminectomy, the opening created in the lamina is in most cases not closed again after the operation. It has been shown that this may prove problematic in the long term as regards mechanical stability and also as regards the rate of complications.

SUMMARY OF THE INVENTION

The object of the invention is to restore the mechanical stability of the vertebra and thus reduce or eliminate the potential problems.

The solution according to the invention lies in the features broadly disclosed herein. Advantageous developments of the invention are the subject matter of the detailed disclosure.

In a bilateral reinforcing implant for the lamina of a vertebra, comprising a transverse support and one anchoring device for the right-hand side and one anchoring device for the left-hand side of the lamina of the vertebra, an expansion element with a guide device and with cheek elements is provided according to the invention, which cheek elements are mounted so as to be longitudinally movable along the guide device, wherein bearing surfaces for the lamina are formed on outer faces of the cheek elements directed away from each other, and at least one of the cheek elements is provided with an aligning device for modifying the orientation of its bearing surface relative to the expansion element.

The invention is based on the concept of using the expansion element acting on the cheek elements in order to securely anchor the reinforcing implant on the resected surfaces produced during the laminectomy. This can be done with elastic widening of the lamina or of the vertebral arch, in order to further increase the fastening reliability in this way. Moreover, in combination with the outward bearing surfaces of the cheek elements, this has the advantage that a collapse of the vertebral arch, as could unfortunately occur hitherto, is rendered impossible. On the contrary, under the pressure hitherto leading to the collapse, the reinforcing implant is only pressed more firmly into its seat and is thus able to meet its purpose. Although the elastic widening in itself can ensure a stable fit in the long term, it is additionally possible to provide a return stop for the cheek elements, in order thereby to further increase the long-term fastening reliability.

The second cheek element is preferably likewise provided with an aligning device. In this way, the second cheek element can also be modified in terms of the orientation of its outer face relative to the guide device. This permits a more precise adaptation of the reinforcing implant to the actual anatomical conditions following the laminectomy. In particular, it allows the bearing surfaces of the cheek elements to be oriented in a wedge shape relative to each other while still fastening the implant as a whole in a manner free from tilting.

The return stop is advantageously designed as a clamping device acting between the cheek elements and the guide device. With such clamping, the expansion position achieved can be easily fixed after the expansion. This avoids slipping of the cheek elements. Should the safety demands as regards undesired movements of the cheek elements be higher, then the return stop can preferably be provided with locking elements, which are arranged between the cheek elements and the guide device. The locking means expediently comprise a ribbing and catches engaging in the latter. With this locking action, achieved by the ribbing in combination with the catch, a secure form-fit connection is made. This affords the advantage of achieving a sufficiently secure hold of the reinforcing implant even in the case of very active patients with corresponding loading of the spinal column.

It has proven useful if the expansion element has at least one area protruding laterally beyond the cheek elements. Thus, independently of the actual expansion position, it is ensured that the reinforcing implant with its cheek elements can be inserted into the opening created by the laminectomy only to such an extent that the bearing surface of the guide device facing the cheek elements bears on the lamina. This prevents the reinforcing implant from being inserted too far and with undesired consequences in terms of the nerves extending through the hollow space being subjected to pain or even in terms of these nerves being damaged or injured.

The guide device is preferably designed as a non-circular bar. Here, non-circular is understood as meaning that the bar does not have a circular cross section. By virtue of this non-circular design, the cheek elements guided on the guide bar are prevented from undesired twisting through a form fit. The bar is advantageously V-shaped, preferably forming a V angle of 10° to 20° at the center. A V angle of 20° has proven particularly useful. In this way, the guide bar fits particularly favorably into the anatomy of the rear of the vertebra. In particular, it barely juts out at all in this way, such that irritation of surrounding tissue is reduced to a minimum.

Provision can also be made that the guide device comprises a fork-shaped rail and a slide guided in the fork interspace. The guide is in this way enclosed and protected against damage, and irritation of the surrounding tissue is avoided. Advantageously, the slide is guided on the rail in such a way that the side ridges engage with a form fit in a pair of grooves. The arrangement will in most cases be such that a pair of grooves facing each other are arranged on the fork-shaped rail, while corresponding and complementary side ridges are arranged on opposite lateral sides of the slide and engage with a form fit in the grooves and guide the slide in a longitudinally movable manner therein. However, the reverse arrangement is also conceivable.

In principle, the slide can be moved by an externally applied movement. However, provision can also be made that a drive device for the slide is provided, which drive device bears on the rail. This drive device can in particular be a screw spindle or a toothed rack. In the latter case, an edge of the rail facing the slide is designed as a toothed rack, while a pinion meshing with the toothed rack is arranged on the slide. By rotation of the pinion, the slide then moves along the rail. It is not absolutely necessary that the pinion is arranged permanently on the slide, and instead it may suffice for the pinion to be temporarily provided for adjustment on the slide. A bore for bearing the pinion is preferably provided on the slide. Practical handling can be made even easier if the drive device is self-locking. This is understood as meaning that, without application of an adjustment force, the drive device does not automatically move under the influence of a force acting on the slide; this means in particular that, when the drive device is not actuated, the expansion element cannot be pressed together, and instead such a movement is blocked by the self-locking. In this way, the position reached upon the adjustment can be secured additionally to the securing by a return stop, in particular a clamping device.

The bearing surfaces on the cheek elements preferably have pointed protuberances (spikes). Proven shapes of such spikes are, for example, conical tips, pyramids, prismatic or V-shaped elevations. Secure primary fixation can be achieved in this way. In order to additionally achieve a rapid and reliable secondary fixation, the bearing surfaces are preferably provided with a coating that promotes bone growth. This can in particular be hydroxyapatite or other osteo-inductive substances.

The bearing surfaces are preferably arranged on the two cheek elements in such a way as to be flush with one another. This is understood as meaning that they do not have a horizontal or vertical offset as seen in the direction of the adjustment path of the expansion element. This avoids an asymmetrical force being applied to the reinforcing implant, with the result that there are no undesired torques acting on the reinforcing implant and seeking to turn it from its intended position.

At least one fixing tongue is advantageously arranged on the cheek elements. It is expediently designed such that, in the implanted state, it bears on an outer surface of the pars of the vertebra. The angle of the fixing tongue in relation to the cheek element can preferably be modified in order to achieve a good bearing contact in accordance with the individual anatomy. This can be achieved in a practical and effective manner by a flexible design of the fixing tongue, preferably with a reduced material thickness in the area of the transition between fixing tongue and cheek element.

The fixing tongue advantageously has a receiving opening for a fastening device. The receiving opening is expediently designed for the polyaxial mounting of a pars screw. Polyaxial is understood as meaning that the screw, with its head, has a secure planar contact in the area of the receiving opening not only in a central position, but also at angle deviations of up to 15° in each direction. In this way, even with a different anatomy of the vertebra, the pars screw can always be inserted in an orientation favorable to fastening. The fastening reliability improves as a result. The receiving opening is preferably oblong and has a plurality of defined receiving positions for the fastening device. The defined receiving positions make it possible to provide different positions for the fastening device (in particular a screw) in relation to the fixing tongue. For this purpose, several dividing lugs are expediently provided, such that a pars screw is mounted with a form fit in each receiving position, which is not the case in a purely oblong hole. In this way, the pars screw can be arranged not only with a translational degree of freedom but also with two rotational degrees of freedom in relation to the fixing tongue, which permits reliable fastening even in difficult anatomical situations.

Receiving couplings for a spreading instrument are expediently provided on the expansion element. These can in particular be locating holes designed as blind bores. By means of these locating holes, the spreading instrument can be coupled quickly and easily to the expansion element. For this purpose, spreading arms of the spreading instrument are preferably provided with complementary carriers for the receiving coupling. A kind of quick-action coupling is thus formed which, in a particularly simple and convenient manner, permits a rapid connection between spreading instrument and implant.

The spreading instrument is expediently designed as a spreading forceps comprising a shaft and a handle. With a spreading forceps, the expansion element can be actuated comfortably and in a manner almost transparent to the operating surgeon. A transmission mechanism is expediently provided between shaft and handle and increases the course of an actuating movement introduced on the handle. For this purpose, the transmission mechanism is expediently provided with a double-action, L-shaped lever, of which the pivot point divides the lever in the ratio of at least 2:1.

It has proven useful if the transmission mechanism is arranged in the shaft. Such an arrangement of the transmission mechanism saves space and thus also permits use in confined conditions without damage to the surrounding tissue. The transmission mechanism is advantageously designed such that the spreaders execute a linear movement. Thus, compared to a conventional rotatory spreading movement, it is possible to achieve more exact guiding of the elements of the expansion element, in particular of the slide.

The danger of jamming, as would arise in the case of spreaders guided in an arc of a circle, can be countered in this way.

A drive instrument is preferably provided, which comprises a shaft with a coupling head at one end and with a handle at the other end, and also an angle marking facing the side. With such a drive instrument, the reinforcing implant can be easily and safely actuated even at its intended implantation site and can be brought into a desired clamping position. In particular, with the angle marking, it is possible to actuate a drive device (for example with a toothed rack) over a defined course, simply by means of a defined angle difference occurring upon actuation of the drive instrument. This heightens the reproducible nature of the spreading procedure, and it also allows less experienced operating surgeons to determine the expansion course in a reproducible manner. Angle marking and handle are advantageously combined with each other. This permits a particularly space-saving construction of the drive instrument.

BRIEF DESCRIPTION OF THE DRAWINGS

The invention is explained in more detail below on the basis of an illustrative embodiment and by reference to the attached drawing, in which:

FIGS. 1 a, b: show a perspective view of a first illustrative embodiment in the disassembled state and the assembled state;

FIGS. 2 a, b: show a perspective view of a second illustrative embodiment in the disassembled state and the assembled state;

FIGS. 3 a, b: show a perspective view of a third illustrative embodiment in the disassembled state and the assembled state;

FIGS. 4 a-d: show a perspective view of a fourth illustrative embodiment in the disassembled state and the assembled state;

FIGS. 6 a-c: show different steps in the gripping of the implant;

FIGS. 7 a, b: show a drive for a reinforcing implant; and

FIGS. 8 a-c: show a view of vertebrae with the reinforcing implant.

DETAILED DESCRIPTION OF THE INVENTION

Figure 1:
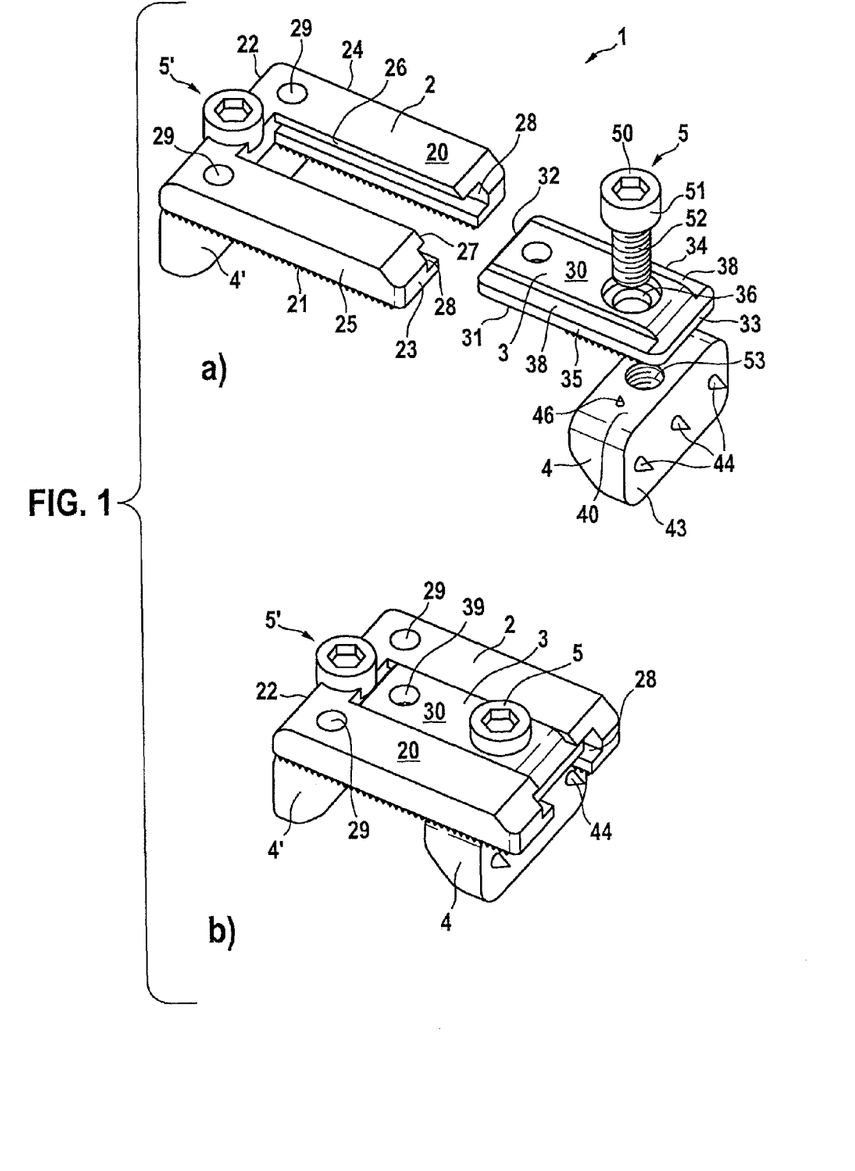

FIG. 1 depicts a first illustrative embodiment of a reinforcing implant according to the invention, which is designated in its entirety by reference number 1 and is a so-called fork variant. The reinforcing implant has, as guide device, a fork-shaped slide bracket 2, in which a carriage 3 is guided in a longitudinally movable manner. Cheek elements 4, 4' are arranged on the slide bracket 2 and on the carriage 3. On their outer faces, i.e. the faces 43 directed away from each other, they have a bearing surface for a lamina of the vertebra.

The fork-shaped slide bracket 2 and the carriage 3 cooperate in such a way that the carriage 3 is guided in a longitudinally movable manner on the slide bracket 2. In this way, an expansion element 1 is formed that can adjust the distance between the two outer faces 43 of the two cheek elements 4 to different sizes. This adjustability makes it possible, by means of the expansion element and through movement of the carriage 3 along its guide on the fork-shaped slide bracket 2, to create a reinforcing implant that can bridge gaps of different widths in the lamina of a vertebral body that have been produced by resection.

The fork-shaped slide bracket 2 has a top surface 20, an underside 21, beveled ends 22, 23, and substantially plane lateral surfaces 24, 25. Guide surfaces 26, 27, along which the carriage 3 is movable, are formed in the fork interspace parallel to the lateral surfaces 24, 25. For more precise and more secure guiding, each of the guide surfaces 26, 27 is formed with a guide groove 28 extending parallel to the underside 21. This is open toward the end 23 and leads, in the transition area, into the bevel of said end.

The carriage 3 is plate-shaped in its basic configuration and has two ends 32, 33 and two lateral surfaces 34, 35. A longitudinal ridge 38 arranged on each of the two lateral surfaces 34, 35 has a shape matching the guide grooves 28 and is dimensioned such that it is received in the latter with a form fit and minimal play. Near the end 33, the carriage 3 is also provided with a through-opening 36, in which a clamping device 5 is arranged for positioning and securing one of the cheek elements 4. The other cheek element 4' is arranged at the other end of the expansion element 1 in the area of the end 22 and is secured by means of a similar type of clamping element 5'. In the illustrative embodiment shown in FIG. 1, the clamping element 5' of the associated cheek element 4' is arranged in the area of a bridge of the fork-shaped slide bracket 2.

The cheek elements 4, 4' are constructed with mirror symmetry to each other (they can also be designed identically to each other). On their outer faces 43 directed away from the respective other cheek element 4', 4, they each have a plurality of spikes 44 for anchoring in the resected surfaces of the lamina. The outer faces 43 with the spikes 44 are preferably provided with a coating, such as hydroxyapatite, that promotes bone growth. On their top surface 40 directed toward the underside 21, 31 of the fork-shaped slide bracket 2 and of the carriage 3, respectively, the cheek elements 4, 4' are preferably provided with a further spike 46, generally a spike 46 of smaller dimensions. This spike 46 is designed to cooperate with the underside 21, 31, which preferably has a ribbing, in such a way that, under the action of a clamping force applied by the clamping device 5, an extremely firm and preferably form-fit connection is established between the cheek elements 4, 4' and the fork-shaped slide bracket 2 and the carriage 3. By means of the clamping device 5, 5' the cheek elements 4, 4' are drawn with their top surface 40, and the spike 46 arranged on the latter, against the ribbing on the underside 21, 31. For this purpose, the clamping device 5, 5' has a screw, which is designated in its entirety by reference number 50 and which comprises a screw head 51 and a shank 52 with an external thread. The head 51 has a greater diameter than the through-opening 36 in the carriage 3, such that the shank 52 can engage through said opening into a corresponding mating thread 53 in the cheek element 4, 4'. By tightening of the screw 50, the cheek element 4, 4' is thus drawn against the underside 31 of the carriage 3 and in a corresponding manner against the underside 21 of the fork-shaped slide bracket 2. This results in a force-fit and also a form-fit connection.

The cheek element 4, 4' arranged on the carriage 3 has, on its outer face 43, a greater dimension than the distance between the lateral surfaces 34, 35 of the carriage 3. In this way, the cheek element 4, 4' protrudes beyond the area of the carriage 3 and is thus drawn by the clamping device 5 not only against the underside 31 of the carriage 3 but also against the underside 21 of the fork-shaped slide bracket 2. The effect of the clamping force thus fixes the relative position between the carriage 3 and the fork-shaped slide bracket 2, that is to say the respective position of the expansion element 1. In this way, it is not only possible to provide a form-fit connection to secure the cheek element 4, 4' against undesired relative twisting about the axis of the screw 50 of the clamping element 5, it is also possible to prevent an undesired return movement of the carriage 3 by the effect of a compressing force acting on the cheek elements 4, 4' through the form-fit engagement of the spikes 46 in the corresponding ribbing on the underside 21 of the slide bracket 2. In this way, securing against twisting and also at the same time against return movement is achieved by a simple construction.

Figure 5:
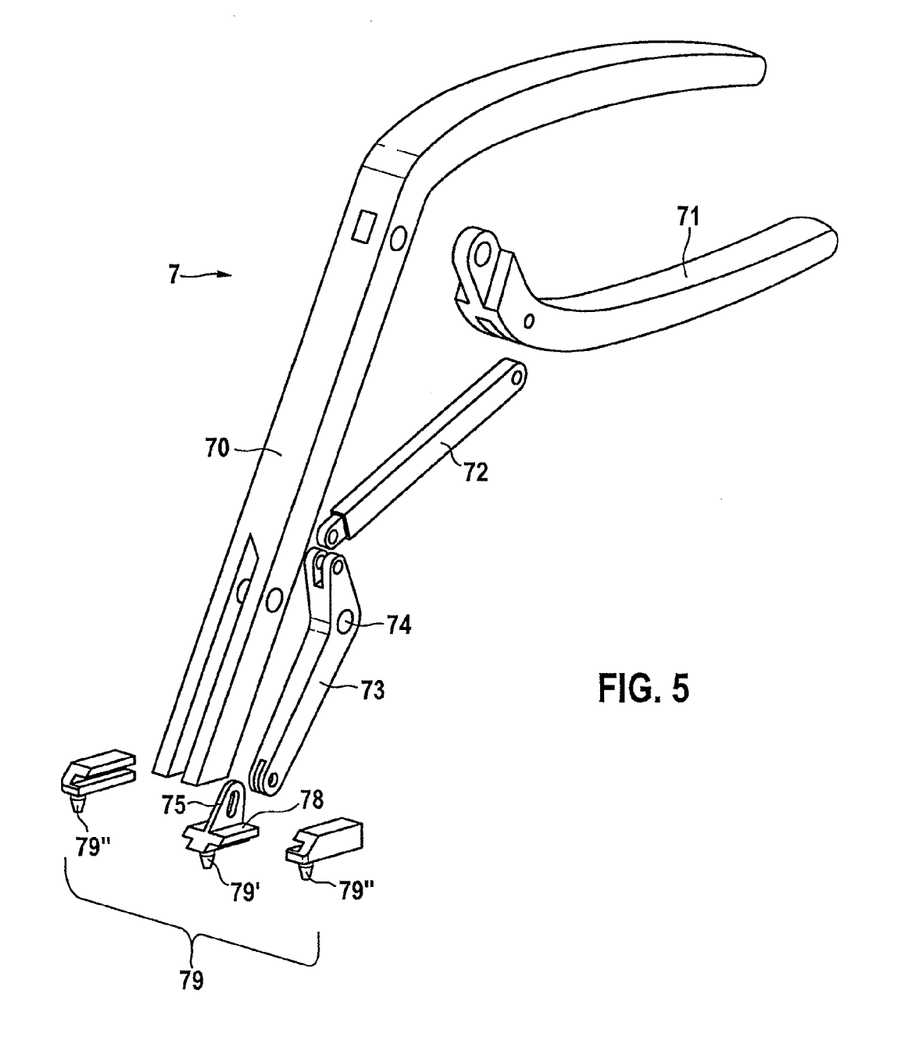
FIG. 5: shows an exploded view of a gripping tool for the reinforcing implant.
Figure 6:
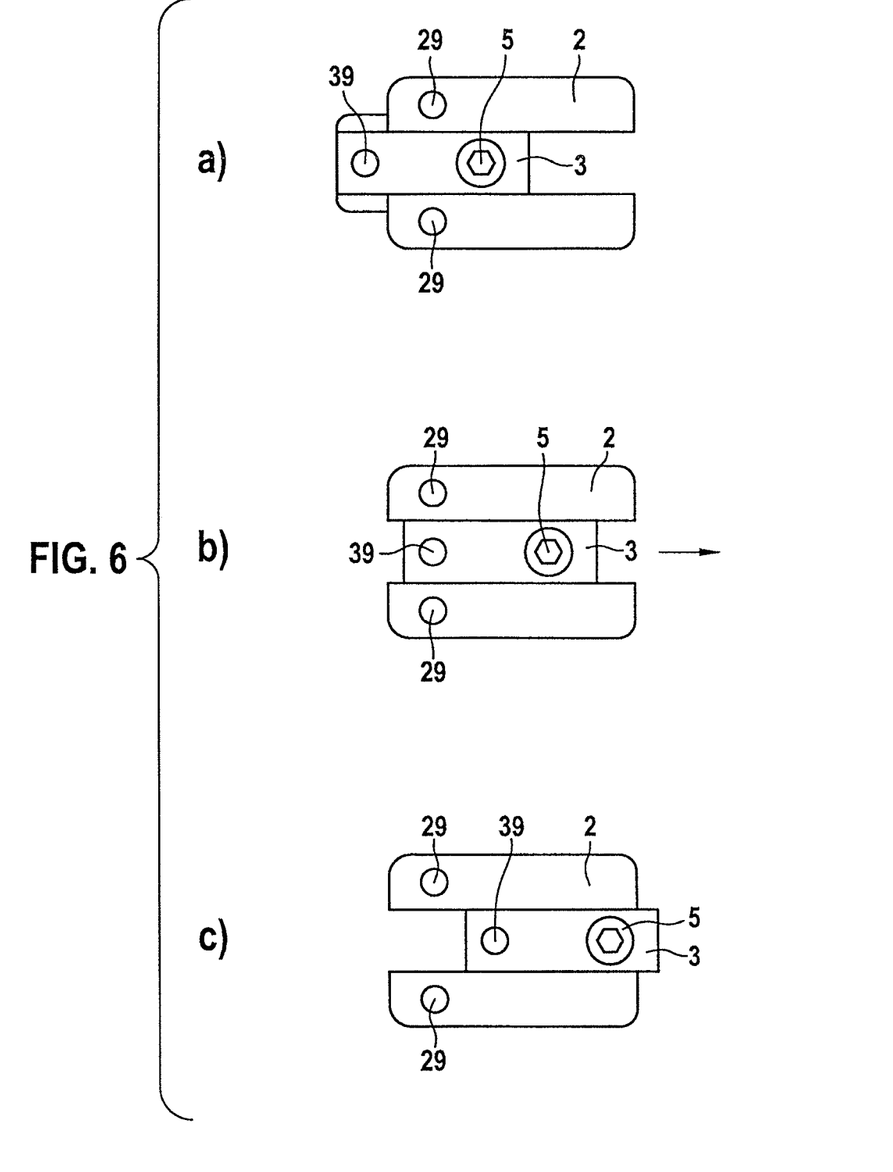

In order to actuate the expansion element 1, a spreading instrument 7 is provided (see FIG. 5) which moves the carriage 3 along the track defined by the grooves 28, and relative to the fork-shaped slide bracket 2, in such a way that the distance between the cheek elements 4, 4' increases. To be able to do this from the direction of the top, the top surfaces 20, 30 of the fork-shaped slide bracket 2 and carriage 3, respectively, are provided, near their ends 22, 32, respectively, with at least two receiving openings 29, 39, respectively, designed as locating bores. In the embodiment shown in FIG. 1, two receiving openings 29 are arranged on the two fork-forming outer elements of the fork-shaped slide bracket 2, and one receiving opening 39 is arranged on the carriage 3. The receiving openings 29 are designed as locating holes for carriers arranged on a tip of the spreading instrument 7. These are designed as cylindrical stubs 79, of which two are arranged rigidly with respect to a shaft 70 of the instrument 7 and one is arranged on a longitudinally movable pusher member 78 of the instrument 7. At the end of the shaft 70 remote from the stubs 79, the instrument 7 has an actuating grip 71, which is mounted pivotably on the shaft 70. The actuating grip 71 acts, via a first linking rod 72, on an L-shaped pivot lever 73 whose grip-side end is connected via a pivot bearing to the linking rod 72 and whose front end acts, via a sliding rail bearing 75, on the pusher member 78 in such a way that the latter is moved linearly, specifically such that it is movable transversely with respect to the axis of the stubs 79. In this way, a pivoting movement of the actuating grip 71 is converted into a linear movement of the pusher member 78, in which the stub 79' arranged on the pusher member 78 moves away from the stubs 79" arranged fixedly on the shaft 70. The arrangement of the stub 79' relative to the stubs 79" is chosen such that, in a starting position (without manual force acting on the actuating grip 71), the stubs 79', 79" are all in a line (see FIG. 6a) and, when the actuating grip 71 is moved, the movable stub 79' arranged centrally between the two stubs 79" fixed on the shaft moves out of the line.

Proceeding from the starting position, with the stubs 79" engaging in the receiving openings 29 designed as locating bores on the fork-shaped slide bracket 2, and with the stub 79' engaging in the receiving opening 39 on the carriage 3, increasing movement of the actuating grip 71 results in the carriage 3 being moved away from the fork-shaped slide bracket 2 (see FIG. 6b), as a result of which the distance between the cheek elements 4, 4' increases and the expansion element 1 is thus spread. By actuation of the clamping device 5, the spread position (see FIG. 6c) is fixed and secured against return movement, and therefore the actuating instrument 7 can be removed.

Not only does the form-fit coupling by means of the stubs 79 in the openings 29, 39 function as a quick-action coupling allowing rapid and reliable coupling or separation even without visual monitoring, it also permits, through the form-fit engagement, a positive feedback of force in the sense that the operating surgeon can sense directly from the actuating grip 71 the forces that are produced by the spreading of the cheek elements 4, 4'. He thus acquires precise feedback as regards the pressing force exerted by the cheek elements 4, 4' on the lamina of the vertebra 9. In this way, the operating surgeon can suitably adjust the force applied during implantation.

Figure 2:
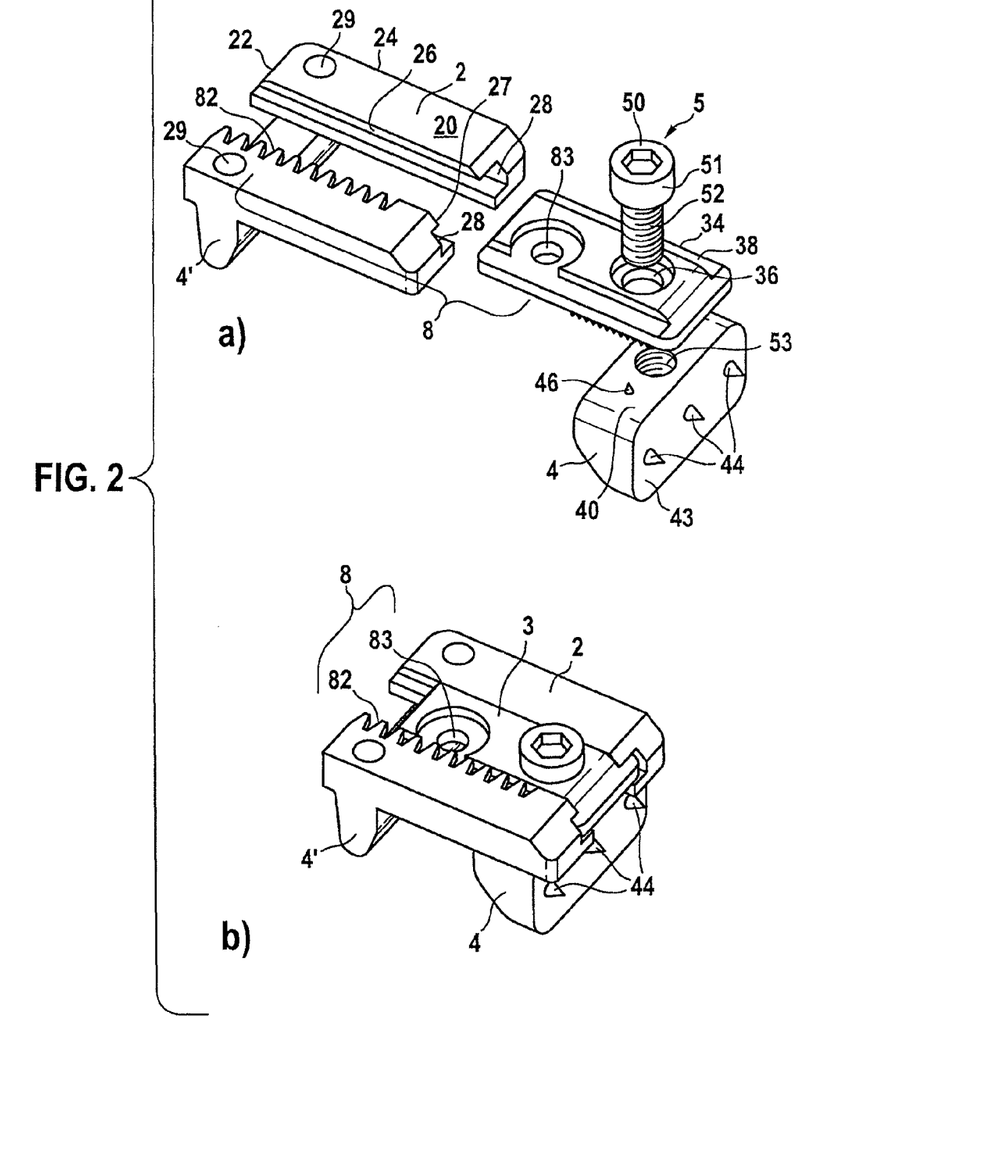
Figure 7:
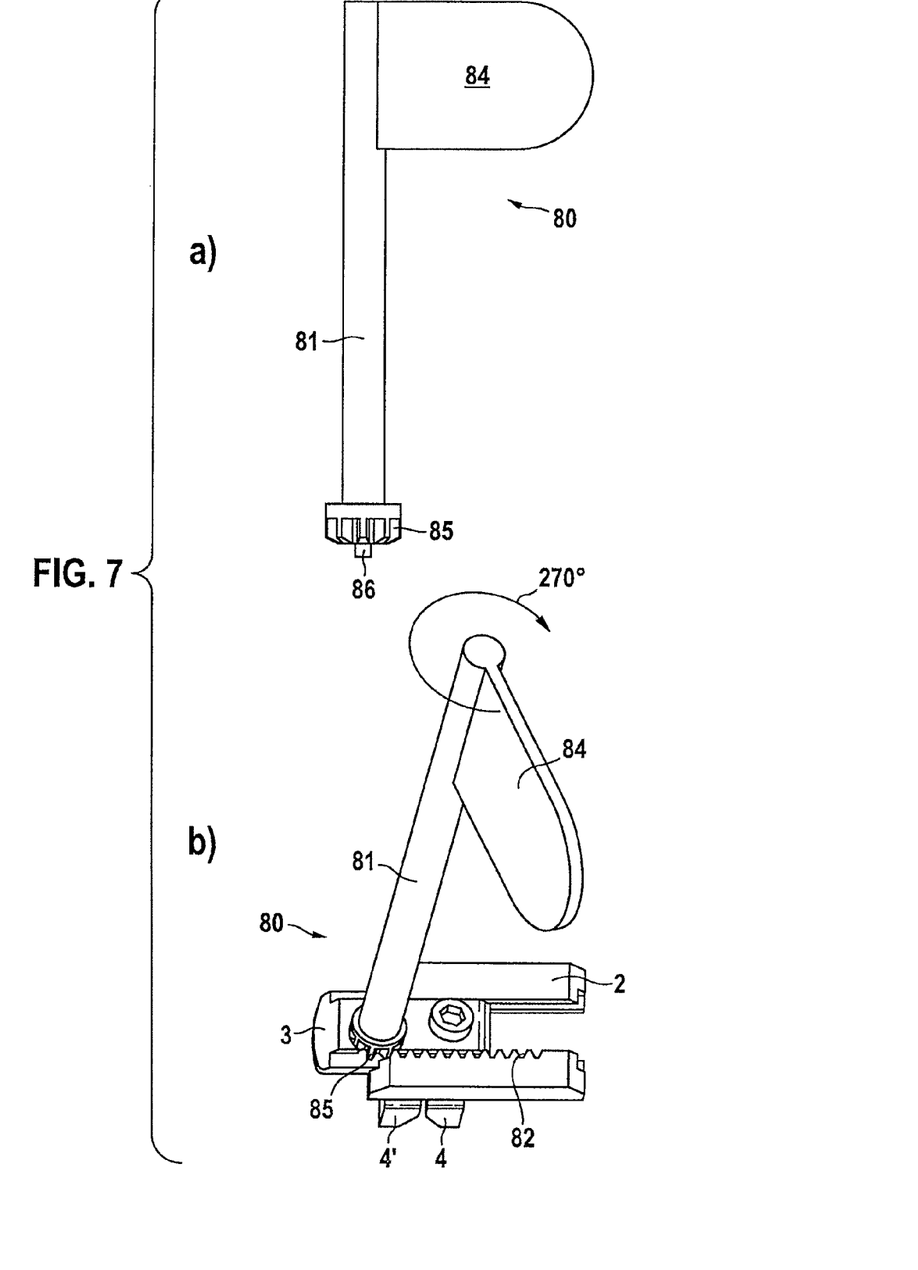

FIG. 2 shows an alternative embodiment, which mainly differs from the embodiment shown in FIG. 1 in that an integrated drive device 8 is provided for spreading the expansion element 1. For this purpose, the carriage 3 is provided with a receiving bore 83 as an abutment for a drive instrument 80 and, furthermore, a toothed configuration 82 is formed on the edge between the top surface 20 and the guide surface 27. This acts as a stationary part of a drive device 8, of which the movable part is formed by the drive instrument 80 (see FIG. 7a) inserted into the receiving bore 83. The drive instrument 80 comprises a shaft 81 with a grip 84 and, formed integrally on the shaft at the other end, a toothed wheel 85, which is provided with a pin stump 86. For actuation, the drive instrument 80 is fitted with its pin stump 86 into the drive bore 83 of the carriage 3, as a result of which the toothed wheel 85 comes into engagement with the toothed configuration 82 on the fork-shaped slide bracket 2. The drive device 8 is actuated by means of the drive instrument 80 being rotated from a starting position by way of the grip 84, as a result of which the toothed wheel 85 meshing with the toothed configuration 82 moves with the carriage 3 along the toothed configuration 82, and the cheek element 4 arranged on the carriage 3 moves away from the cheek element 4' arranged on the fork-shaped slide bracket 2. When the desired distance is reached, then, as in the first embodiment shown in FIG. 1, the clamping device 5 is actuated by tightening of the clamping screw 50, and the carriage is thus fixed in the position that it has reached. The drive instrument 80 can then be removed.

As in the first embodiment, the attainment of the desired position can be defined as being when a defined adjustment force is achieved. However, there is also the possibility of using a defined adjustment travel as the criterion, which can be set simply by an actuating angle of the drive tool 8. In this respect, the grip 84 functions as an angle index. When the drive instrument 80 is inserted in a normal position, and if an adjustment travel corresponding to a rotation of 270° is provided, it is thus actuated by rotation until the grip 84 reaches a three-quarter turn corresponding to 270°. In this way, the desired adjustment is achieved, and therefore also the desired distance between the two cheek elements 4, 4'. A reproducible adjustment of the implant can thus be achieved even under different conditions of use.

It will be noted that the second embodiment, shown in FIG. 2, does not necessarily have to be adjusted by means of the drive device and the associated drive instrument 80, and instead a receiving coupling for a gripping tool can likewise be provided, that is to say, as in the first embodiment, with locating bores 29 on the fork-shaped slide bracket 2' and a corresponding locating hole 39 on the carriage 3'.

Figure 3:
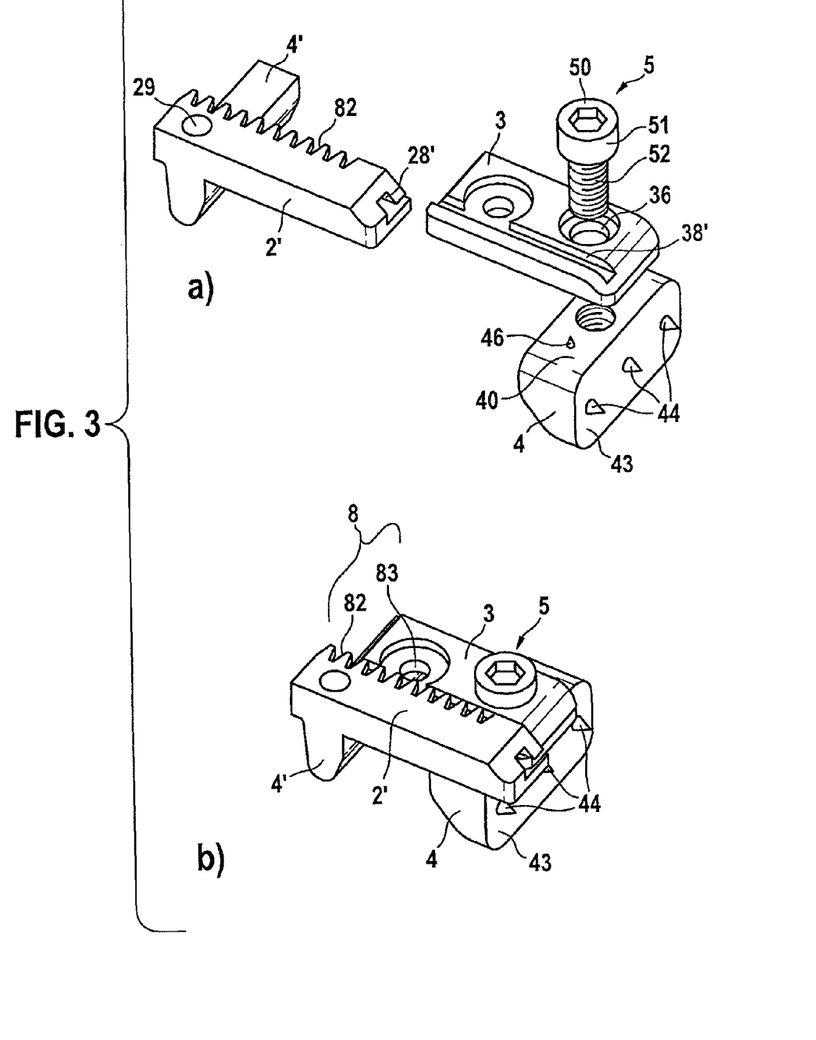

FIG. 3 shows a third embodiment which, in contrast to the first two embodiments, does not have a fork-shaped slide bracket, but instead a one-sided slide bracket 2'. The guide groove 28' has an upwardly directed undercut, in which a hook continuation of the longitudinal ridge 38' engages and thus holds the carriage 3 on the one-sided slide bracket 2'. This embodiment is designated as "monorail".

Figure 4:
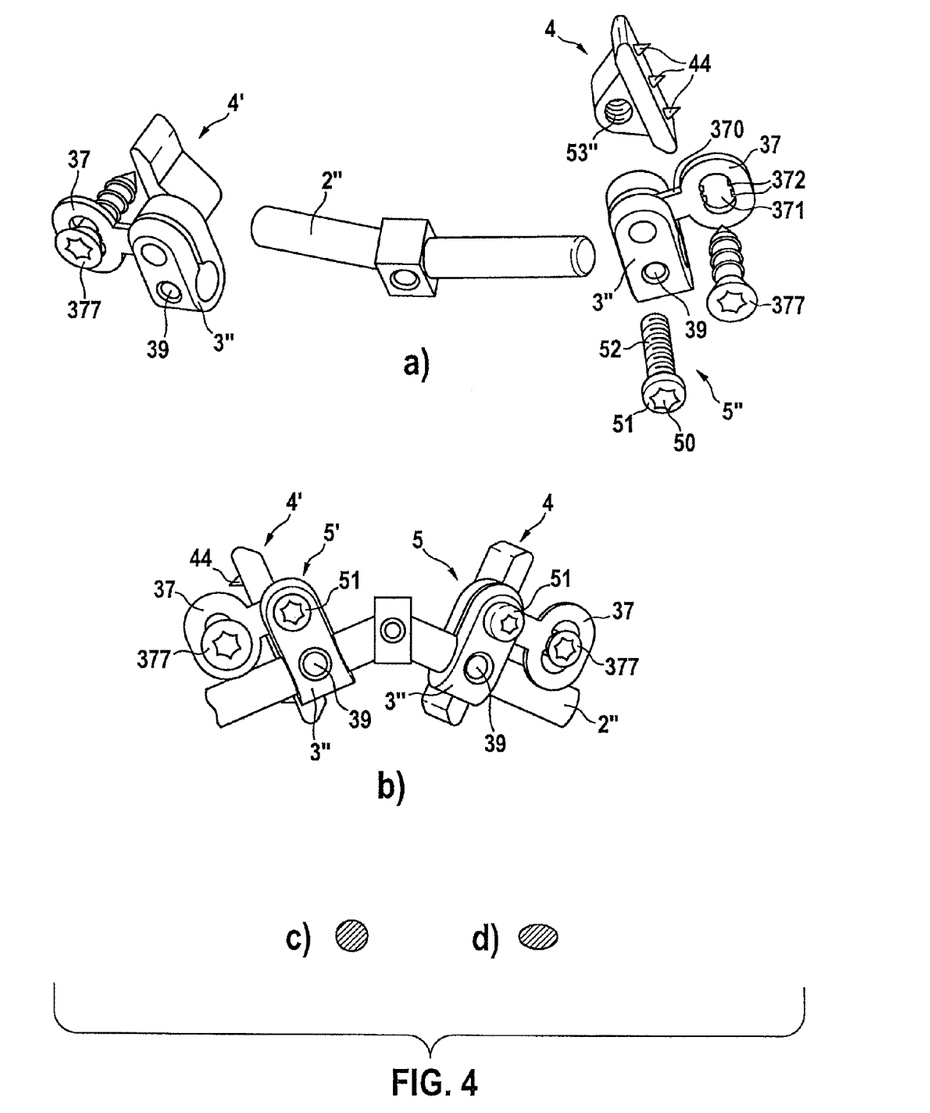

A fourth embodiment, shown in FIG. 4, mainly differs from the embodiments shown in FIGS. 1 to 3 in that it is in a skeleton construction. The slide piece is in this case designed as a straight bar or V-shaped bar (the latter is shown in FIG. 4). It functions as a support for two sliding carriages 3", which are fitted onto and are guided in a longitudinally movable manner on the bar 2". Moreover, the bar 2" has a non-circular cross section, in the illustrative embodiment shown an oval cross section (see FIG. 4d), and thus secures the sliding carriages 3" against twisting with respect to the bar 2". For this purpose, the sliding carriages 3" each have a through-opening congruent with respect to the cross-sectional shape of the bar 2". This through-opening is part of a clamp, which is actuated by a clamping device 5". This comprises a screw 50 which is mounted with its head 51 on one side of the clamp and cooperates with a mating thread 53" arranged on the other side of the clamp. By tightening of the screw 50, the clamp is actuated and the respective sliding carriage 3" is thereby fixed relative to the bar 2". It will be noted that the non-circular cross section is not essential, and instead the cross section can also be round (see FIG. 4c).

In order to actuate the expansion element thus formed, receiving couplings for the gripping tool 7 are once again formed on the sliding carriages 3". For this purpose, as in the aforementioned illustrative embodiments, the sliding carriage 3" in each case has a locating bore 39, but, in contrast to the aforementioned embodiments, the bar 2" does not need to have any locating bore. The spreading tool 7 is fitted with one of its stationary stubs 79" into one of the locating bores 39 and with its movable stub 79' into the other locating bore 39, as a result of which, when the spreading tool is actuated, the two sliding carriages 3" are moved away from each other along the guide defined by the bar 2". When the desired position is reached, it is secured by actuation of the clamping device 5", and the spreading tool 7 can be removed.

As in the embodiments described above, the cheek elements 4, 4' are held by means of the clamping device.

In order to better fix the implant on the vertebra, a fixing tongue 37 is provided, which is arranged jutting out from the sliding carriages 3". It will be noted that such a fixing tongue 37 can also be provided in the other embodiments; it is explained in more detail below in respect of the embodiment shown in FIG. 4, and this explanation applies analogously to the other embodiments. The fixing tongue 37 is provided with a reduced material thickness 370 in the area of the transition to the sliding carriage 3". By virtue of this reduced material thickness 370, the fixing tongue 37 can be bent in order to modify its angle position relative to the sliding carriage 3". This permits adaptation to the particular anatomical conditions of the vertebra, in order to achieve optimized bearing of the fixing tongue 37 on the vertebra, or more precisely on the pars thereof. At its free end, the fixing tongue 37 is provided with a fastening opening 371. The latter is preferably elongate and, along its two long sides, is divided into three areas by two projections 372. The edge of the fastening opening 371 is shaped obliquely in order to provide, together with the projections 372, a conical contact surface. A pars screw 377 with a round receiving head can thus be mounted in a total of three positions in the fastening openings 371: an upper position, a middle position between the pairs of projections 372, and a lower position. The pars screw 377 is thus mounted in one of the positions in the fastening opening 371 of the fixing tongue 37 such that it can assume different axes (polyaxial) in two directions and through ±15°. The dimensions of the fastening openings 371 are chosen such that the different positions each lie 2 mm apart, that is to say an overall adjustment of 4 mm is permitted by the three positions.

Figure 8:
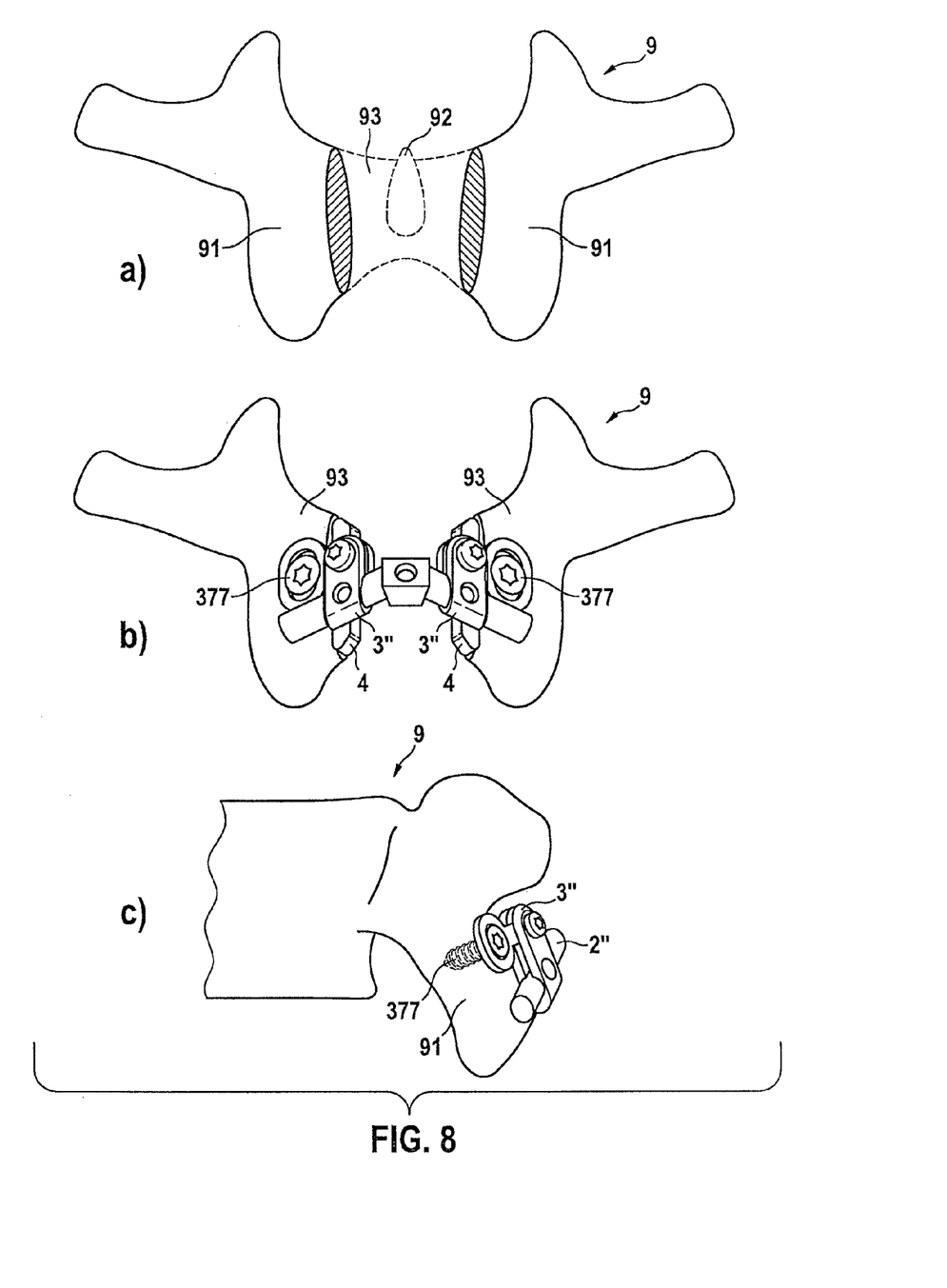

FIGS. 8a, b show an example of the arrangement of the implant in a vertebra 9. FIG. 8a is a rear view of the vertebra 9 with a lamina 93, where a spinous process 92 and adjoining areas to the right and left of the latter have been removed by resection (indicated by broken lines). The implant is inserted into the opening thus formed in the lamina 93 and, as has been described above, the expansion element 1 is moved apart such that the cheek elements 4, 4' of the implant come to bear on the sectioned surfaces (shown by hatching in FIG. 8a) that have been produced during the resection of the lamina 93 and are braced against these surfaces. The implant thus forms a bridge connecting the two ends of the lamina 93. The spikes 46 on the outer faces 43 of the cheek elements 4, 4' engage in the sectioned surfaces on the lamina 93 and thus provide primary fastening of the implant. In order to further protect the implant against dislocation and against undesired twisting, further anchoring is provided on both sides by the fixing tongue with the pars screw 377, specifically in the pars 91 of the vertebra 9. The latter is symbolized for illustrative purposes in the partially cutaway view in FIG. 8c.

The invention claimed is:

1. A reinforcing implant for the lamina of a vertebra, comprising a transverse support and one anchoring device for a right-hand side and one anchoring device for a left-hand side of the lamina of the vertebra, and an expansion element with a guide device and with a plurality of cheek elements mounted so as to be longitudinally movable along the guide device,
   wherein bearing surfaces for the lamina are formed on outer faces of the cheek elements directed away from each other, and a return stop for the cheek elements is provided, wherein at least one of the cheek elements is provided with an aligning device for modifying the orientation of its bearing surface relative to the guide device, and
   further comprising a clamping screw configured to function as a bearing for the aligning device, wherein the aligning device allows an aligning rotation of the cheek element around the bearing and wherein the clamping screw is configured to fasten the cheek element on the implant.

2. The reinforcing implant as claimed in claim 1, wherein the return stop is configured as a clamping device acting between cheek elements and guide device.

3. The reinforcing implant as claimed in claim 2, wherein the return stop has locking elements, which act between cheek elements and guide device.

4. The reinforcing implant as claimed in claim 3, wherein the locking elements comprise a rib and at least one catch engaging therein.

5. The reinforcing implant as claimed in claim 1, wherein a second cheek element is provided with an aligning device.

6. The reinforcing implant as claimed in claim 1, wherein the expansion element has at least one area protruding laterally beyond the cheek elements.

7. The reinforcing implant as claimed in claim 1, wherein the guide device has a non-circular bar, with a recess of complementary shape in the cheek elements.

8. The reinforcing implant as claimed in claim 7, wherein the bar is V-shaped and forms a V angle of 10° to 30°.

9. The reinforcing implant as claimed in claim 1, wherein the guide device comprises a fork-shaped rail and a slide guided in the fork interspace.

10. The reinforcing implant as claimed in claim 9, wherein the slide is guided on the rail via a groove-and-ridge arrangement, with the ridge engaging with a form fit in the groove.

11. The reinforcing implant as claimed in claim 9, wherein a drive device, which bears on the rail, is arranged on the slide.

12. The reinforcing implant as claimed in claim 11, wherein the drive device comprises a toothed rack or a screw spindle.

13. The reinforcing implant as claimed in claim 11, wherein the drive device is self-locking.

14. The reinforcing implant as claimed in claim 9, further comprising a drive instrument which comprises a shaft with a coupling head at one end and with a handle at the other end, and also an angle marking facing the side.

15. The reinforcing implant as claimed in claim 14, wherein the handle and the angle marking are combined with each other.

16. The reinforcing implant as claimed in claim 1, wherein the bearing surface has pointed protuberances.

17. The reinforcing implant as claimed in claim 1, wherein the bearing surface is provided with a coating that promotes bone growth.

18. The reinforcing implant as claimed in claim 1, wherein bearing surfaces on the cheek elements are flush with one another.

19. The reinforcing implant as claimed in claim 1, wherein at least one fixing tongue is arranged on the cheek elements.

20. The reinforcing implant as claimed in claim 19, wherein the fixing tongue has a receiving opening for a fastening element.

21. The reinforcing implant as claimed in claim 20, wherein the receiving opening is configured for the polyaxial mounting of a pars screw.

22. The reinforcing implant as claimed in claim 20, wherein the receiving opening is oblong and is divided by several lugs into a plurality of unambiguous receiving positions for the fastening element.

23. The reinforcing implant as claimed in claim 1, wherein receiving couplings for a gripping tool are provided on the expansion element.

24. The reinforcing implant as claimed in claim 23, wherein the receiving couplings are configured as locating holes.

25. The reinforcing implant as claimed in claim 24, wherein a spreading instrument is provided, of which spreading arms are provided with complementary carriers for the receiving coupling.

26. The reinforcing implant as claimed in claim 25, wherein the spreading instrument is a spreading forceps comprising a shaft and a handle.

27. The reinforcing implant as claimed in claim 26, wherein a transmission mechanism is provided that increases the course of an actuating movement acting on the handle.

28. The reinforcing implant as claimed in claim 27, wherein the transmission mechanism has an L-shaped, double-action lever, of which a pivot point divides the lever arms in a ratio of at least 2:1.

29. The reinforcing implant as claimed in claim 27, wherein the transmission mechanism is arranged in the shaft.

30. The reinforcing implant as claimed in claim 27, wherein the transmission mechanism is designed such that the spreaders execute a linear movement.

* * * * *